US010456365B2

(12) United States Patent
Yamaguchi

(10) Patent No.: US 10,456,365 B2
(45) Date of Patent: Oct. 29, 2019

(54) METHODS AND FORMULATIONS FOR SUPPORTING AND PROMOTING BONE HEALTH

(71) Applicant: Primus Pharmaceuticals, Inc., Scottsdale, AZ (US)

(72) Inventor: Masayoshi Yamaguchi, Shizuoka (JP)

(*) Notice: Subject to any disclaimer, the term of this patent is extended or adjusted under 35 U.S.C. 154(b) by 0 days.

(21) Appl. No.: 15/469,515

(22) Filed: Mar. 25, 2017

(65) Prior Publication Data

US 2017/0273912 A1  Sep. 28, 2017

Related U.S. Application Data

(60) Provisional application No. 62/313,423, filed on Mar. 25, 2016.

(51) Int. Cl.
| | | |
|---|---|---|
| *A61K 31/015* | (2006.01) | |
| *A61K 31/35* | (2006.01) | |
| *A61K 31/59* | (2006.01) | |
| *A61K 33/32* | (2006.01) | |
| *A61K 33/42* | (2006.01) | |
| *A61K 31/366* | (2006.01) | |
| *A61K 31/593* | (2006.01) | |
| *A61K 33/30* | (2006.01) | |
| *A61K 31/352* | (2006.01) | |

(52) U.S. Cl.
CPC .......... *A61K 31/015* (2013.01); *A61K 31/352* (2013.01); *A61K 31/366* (2013.01); *A61K 31/593* (2013.01); *A61K 33/30* (2013.01)

(58) Field of Classification Search
CPC ............................ A61K 31/015; A61K 31/352

USPC ................................................. 514/766, 455
See application file for complete search history.

(56) References Cited

U.S. PATENT DOCUMENTS

| | | | | |
|---|---|---|---|---|
| 7,435,725 | B2 * | 10/2008 | Rosenbloom | A61K 8/42 424/59 |
| 2008/0280996 | A1 * | 11/2008 | Pianowski | A61K 31/015 514/763 |
| 2010/0093678 | A1 * | 4/2010 | Della-Fera | A61K 31/12 514/167 |

OTHER PUBLICATIONS

Ginaldi et al. "Osteoporosis, inflammation and Ageing," Immunity & Ageing, 2005, http://www.immunityageing.com/Content/2/1/14.*
Basha et al. "beta-caryophyllene, a natural sesquiterpene, modulates carbohydrate metabolism in streptozone-induced diabetic rate," Acta Histochemica, 2014 vol. 116, pp. 1469-1479.*
Ho et al., Biochem Pharmacol. Sep. 15, 1999;58(6):983-90. Effects of nonsteroidal anti-inflammatory drugs and prostaglandins on osteoblastic function. (Abstract only).
Guesens et al., Curr Opin Rheumatol. Jul. 2013;25(4):524-31. NSAIDs and fracture healing. (Abstract only).
Morton et al., Journal of Bone and Mineral Research vol. 13, No. 12, 1998, Nonsteroidal Anti-Inflammatory Drugs and Bone Mineral Density in Older Women: The Rancho Bernardo Study.

* cited by examiner

*Primary Examiner* — Shengjun Wang
(74) *Attorney, Agent, or Firm* — Clark G Sullivan

(57) ABSTRACT

Pharmaceutical formulations of β-Caryophyllene, and methods of supporting and promoting bone health using β-Caryophyllene, are described.

13 Claims, No Drawings

METHODS AND FORMULATIONS FOR SUPPORTING AND PROMOTING BONE HEALTH

FIELD OF THE INVENTION

The present invention relates to β-Caryophyllene, methods of supporting and promoting bone health using β-Caryophyllene, and pharmaceutical formulations thereof.

BACKGROUND OF THE INVENTION

Osteoporosis is a common metabolic disease characterized by a decrease in bone mass and a reduction of bone strength. Osteoblasts differentiate bone marrow mesenchymal stem cells and stimulate bone formation and calcification. Adipocytes also differentiate mesenchymal stem cells. There is an inverse relationship between the differentiation of mesenchymal stem cells to osteoblasts and adipocytes. Osteoclasts are developed from hematopoietic progenitors and promote bone resorption. The differentiation of bone marrow mesenchymal stem cells is involved in the development of osteoporosis.

Patients with osteoporosis suffer from a decrease in osteoblastic bone formulation and an increase in osteoclastic bone resorption, which can lead to a dramatic reduction in bone mass. Osteoporosis is more common in women after the beginning of menopause, affecting at least 200 million worldwide, with one third between ages 60 and 70 years and two thirds above age 80. Osteoporosis is recognized as a major public health threat.

Studies have shown that osteoporosis is more prevalent in people with obesity and type 1 and type 2 diabetes. Osteoporotic fractures are common in overweight or obese people, particularly obese men. Secondary causes of osteoporosis include obesity and diabetes, which is associated with bone marrow adiposity. Thus, there is a need for new treatments that inhibit adipogenesis and stimulate osteoblastogenesis to treat osteoporosis, particularly in people with obesity or diabetes.

β-Caryophyllene is a natural sesquiterpene present in the essential oils of many plants such as clove, hemp *Cannabis sativa*, rosemary *Rosmarinus oficinalis*, and hops. β-Caryophyllene has been approved as a food additive by the U.S. Food and Drug Administration (FDA), and is widely used in foods as a flavor and aroma enhancer.

The effects of β-Caryophyllene on inflammation have been known for years. Its effect on bone stem cell differentiation has not been previously known before the present invention.

The aim of this invention is to use β-Caryophyllene to modulate the differentiation of bone marrow cells, and to develop methods and pharmaceutical formulations that can effectively treat osteoporosis and related conditions.

SUMMARY OF THE INVENTION

The inventors have unexpectedly discovered that β-Caryophyllene stimulates osteoblastic mineralization and suppresses osteoclastogenesis and adipogenesis, and based on these discoveries have developed new therapeutic methods and new pharmaceutical compositions. Thus, in a first principle embodiment, the invention provides a method for treating osteoporosis in a human being in need thereof comprising administering to said human being a therapeutically effective amount of β-Caryophyllene.

In a second principle embodiment, the invention provides a method of stimulating osteoblastic mineralization in a human being in need thereof comprising administering to said human being a therapeutically effective amount of β-Caryophyllene.

In a third principle embodiment, the invention provides a method of suppressing osteoclastogenesis or adipogenesis in a human being in need thereof comprising administering to said human being a therapeutically effective amount of β-Caryophyllene.

In a fourth principle embodiment, the invention provides a unit dosage form useful in any of the methods of the present invention comprising therapeutically effective amounts of β-Caryophyllene and a second therapeutic agent that may be genistein, vitamin D3, calcium, zinc, vitamin K2, or a combination thereof.

Additional advantages of the invention are set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of preferred embodiments of the invention and the Examples included therein.

Definitions and Use of Terms

As used in this specification and in the claims which follow, the singular forms "a," "an" and "the" include plural referents unless the context clearly dictates otherwise. Thus, for example, reference to "an ingredient" includes mixtures of ingredients, reference to "a therapeutic agent" includes more than one therapeutic agent, and the like.

"Osteoporosis" refers to a medical condition related to as decrease of bone mass, where bones become increasingly brittle or fragile due to the loss of calcium or vitamin D. Osteoporosis occurs when the creation of new bone does not keep up with the removal of old bone. Osteoporosis-related fractures commonly occur in the hip, wrist, and spine.

"Therapeutically effective amount" means a dose or amount that produces a therapeutic response or desired effect. Therapeutically effective amount refers to the quantity or amount of a substance that is required to correct the manifestations of a particular deficiency.

"Osteoblast" means a cell that synthesizes bone. Osteoblasts arise from mesenchymal stem cells and function in groups in the process of bone formation upon maturation. Specifically, osteoblasts form the functional part of the bone known as the bone matrix, which consists of protein and mineral.

"Osteoblastic mineralization" means the process of mineralization of newly formed bone matrix. Mineral density in the adult skeleton directly influences bone strength. Osteoblasts release small, membrane-bound matrix vesicles that concentrate calcium and phosphate and enzymatically destroy mineralization inhibitors.

"Osteoclastogenesis" is the development of osteoclasts, a type of bone cell that breaks down bone tissue. Osteoclasts are important to the maintenance, repair, and remodeling of bones. Osteoclasts derive from mononuclear precursor cells of the monocyte-macrophage lineage.

"Mesenchymal stem cells" are multipotent stromal cells that can differentiate into a variety of cell types including osteoblasts and adipocytes.

"Adipocytes" are cells specialized for fat storage and found in connective tissue. Adipocytes arise from mesenchymal stem cells in bone marrow.

"Osteoclastic bone resorption" refers to the process in which osteoclasts disassemble bone and digest composite proteins and minerals. In the case of osteoporosis, bone breaks down much faster than it is renewed.

The structure for β-caryophyllene is presented below.

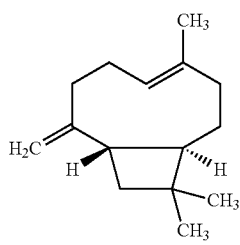

Description of Principal Embodiments

Thus, in a first principle embodiment, the invention provides a method for treating osteoporosis in a human being in need thereof comprising administering to said human being a therapeutically effective amount of β-caryophyllene.

In a second principle embodiment, the invention provides a method of stimulating osteoblastic mineralization in a human being in need thereof comprising administering to said human being a therapeutically effective amount of β-Caryophyllene.

In a third principle embodiment, the invention provides a method of suppressing osteoclastogenesis or adipogenesis in a human being in need thereof comprising administering to said human being a therapeutically effective amount of β-Caryophyllene.

In a fourth principle embodiment, the invention provides a unit dosage form comprising therapeutically effective amounts of β-Caryophyllene and a second therapeutic agent that may be genistein, vitamin D3, calcium, zinc, vitamin K2 or a combination thereof.

Description of Subembodiments

Each of the following subembodiments can be used to further characterize and limit each of the foregoing principal embodiments. In addition, more than one of the following subembodiments can be combined and used to further characterize and limit each of the foregoing principal embodiments, in any manner that is mathematically and physically possible.

In various subembodiments of the foregoing embodiments, the therapeutically effective amount of β-Caryophyllene ranges from about 25 mg to 1,000 mg, from about 50 mg to about 500 mg, from about 75 to about 300 mg, and most preferably about 100 mg, administered on a daily basis.

In additional subembodiments of the foregoing embodiments, the therapeutically effective amount of β-Caryophyllene is effective to support or promote bone health.

In additional subembodiments of the foregoing embodiments, the therapeutically effective amount of β-Caryophyllene is effective to treat osteoporosis.

In additional subembodiments of the foregoing embodiments, the therapeutically effective amount of β-Caryophyllene is effective to suppress differentiation of mesenchymal stem cells to adipocytes.

In any of the foregoing principal embodiments, the therapeutically effective amount of β-Caryophyllene is effective to favor osteoblastic bone formulation over the inhibition of osteoclastic bone resorption.

In any of the foregoing principal embodiments, the therapeutically effective amount of β-Caryophyllene is effective to favor osteoblastic bone formulation over the suppression of osteoclastogenesis or adipogenesis.

In any of the foregoing principal embodiments, the therapeutically effective amount of β-Caryophyllene is effective to prevent osteoporosis involved in obesity and diabetes.

In any of the foregoing embodiments, the therapeutically effective amount of β-Caryophyllene can be administered with a second therapeutic agent which is also effective to support or promote bone health, to suppress differentiation of mesenchymal stem cells to adipocytes, to favor osteoblastic bone formulation over the inhibition of osteoclastic bone resorption, to favor osteoblastic bone formulation over the suppression of osteoclastogenesis or adipogenesis, or to treat or prevent osteoporosis in obesity or diabetes.

Particularly useful second agents include genistein, vitamin D3, calcium, zinc, vitamin K2 and combinations thereof.

The formulations of the present invention can be provided in any dosage form that is suitable for oral administration, including tablets, capsules, liquids, orally dissolving tablets, and the like.

It is preferred that the dosage is orally administered. Suitable oral dosage forms include, for example, tablets, capsules, or caplets prepared by conventional means with pharmaceutically acceptable excipients such as binding agents, fillers, lubricants, disintegrates, or wetting agents.

Further, it is preferred that the doses be administered once or twice daily. When administered twice daily, one half of the daily dose will preferably be administered with each dose. Representative daily doses of the second active agent are set forth below:

Genistein: 10 to 120 mg, 20 to 75 mg, or 40 to 60 mg, or 54 mg;
Vitamin D3: 50 to 1500 IU, 100 to 1000 IU, 150 to 600 IU, or 400 IU;
Zinc: 1 to 30 mg, 10 to 20 mg, or 16 mg;
Vitamin K2: 10 to 100 mg, 20 to 80 mg, or 45 mg.

Representative formulations for use in the present invention include:
a) From about 50 to about 300 mg of β-Caryophyllene; and, optionally, one or any combination of the following ingredients:
b) about 27 or 54 mg of genistein;
c) about 200 or 400 IU of vitamin D3;
d) about 8 or 16 mg zinc; and
e) about 22.5 or 45 mg of vitamin K2.

Experiments Conducted

Various experiments were conducted to determine the effect of β-Caryophyllene on C57BL/6 in vitro. C57BL/6 cells refer to mesenchymal stem cells in bone marrow from female 2-month old mice (C57BL/6).

Materials

The following materials were used during the experiments: C57BL/6 cells, Dulbecco's Modification of Eagle's Medium (DMEM) with fetal bovine serum (FBS), penicillin-steptomycin, dexamethasone, 3-isobutyl-q-methylxanthine, and β-Caryophyllene. Medium was replaced with DMEM containing insulin.

Cell Proliferation

C57BL/6 cells were prepared as 1×10$^6$/ml per well. These cells were cultured using 12-well plates in DMEM containing 10% FBS, 1% penicillin-steptomycin in the presence or absence of dexamethasone (1 μM/ml) and 3-isobutyl-q-methylxanthine (0.5 mM/ml) with either vehicle or β-Caryophyllene (0.1-100 μM). Medium was replaced containing insulin (10 μg/ml) without dexamethasone and 3-isobutyl-q-methylxanthine, with either the presence or absence of β-Caryophyllene (0.1-100 μM) for four days in $CO_2$ incubator (37° C.). In other experiments, the cells were cultured without β-Caryophyllene for an additional four days. After culture, the adipocytes were stained and counted.

Adipogenesis in Bone Marrow Cell Culture

Bone marrow cells (1×10$^6$ cells/well/ml in 12-well plates) were cultured for 3 days in DMEM containing 10% FBS, 1% penicillin-streptomycin (P/S; 10,000 U/L) in the presence or absence of the differentiation medium (DM) [dexamethasone (1 μM/ml of medium) and 3-isobutyl-1-methylxanthine (IBMX; 0.5 mM/ml of medium)] with either vehicle or β-caryophyllene (0.1-100 μM). Medium was replaced with DMEM (containing 10% FBS and 1% P/S) containing insulin (10 μg/ml of medium) without dexamethasone and IBMX, and the cells were cultured in the presence or absence of β-caryophyllene (0.1-100 μM) for an additional 4 days in $CO_2$ incubator (37° C.). In other experiments, the cells were cultured in DM for 3 days with or without β-caryophyllene (0.1-100 μM), and then medium was replaced and cells were cultured in medium containing insulin (10 μg/ml of medium) for additional 4 days without β-Caryophyllene. After culture, the medium was removed, and adipocytes were stained with Oil Red O. Adipocytes were counted by light microscopy. For quantification, the dye was extracted with 0.2 ml of isopropanol for 1 minute, and the absorbance (490 nm) was read using a Spectra Count microplate photometer.

Mineralization in Bone Marrow Culture

C57BL/6 cells were prepared as 1×10$^6$/ml per well in 12-well plates. Cells were cultured in either the presence or absence of DMEM with mineralization medium containing ascorbic acid (100 μg/ml) and 4 mM β-glycerophosphate in DMEM with 10% FBS and 1% penicillin-steptomycin. Cells were cultured with either vehicle or β-Caryophyllene (0.1-100 μM) for 18 days at 37° C. in humidified 5% $CO_2$ atmosphere. After culture, the cells were washed and stained. After elution with 10% cetylpyridinium chloride solution, the absorbance at 570 nm on a microtiter plate reader.

Osteoclastogenesis in Bone Marrow Cell Culture

C57BL/6 cells were prepared as 2×10$^5$/ml per well in 24-well plates. Cells were cultured in DMEM with 10% FBS and 1% penicillin-steptomycin in water-saturated atmosphere containing 5% $CO_2$ and 95% air at 37° C. Cells were cultured with or without Tumor necrosis factor-α (5 ng/ml) for 3 days in the presence or absence of β-Caryophyllene (0.1-100 μM). Medium was replaced and cultures were maintained for an additional 4 days. In other experiments, the cells were cultured for 3 days and then placed in medium without β-Caryophyllene for an additional 4 days. Cells were stained with a marker enzyme of osteoclasts and washed with phosphate buffered sale solution and foxed with 10% neutralized formalin-phosphate for 10 minutes. The cells were stained with TRACP staining and incubated for 90 minutes. TRACP—positive cells containing three or more nuclei were counted as osteoclast-like cells.

Statistical Analysis

Statistical significance was determined with GraphPad InStat version 3 for Windows XP (GraphPad Software Inc. La Jolla, Calif.). Multiple comparisons were performed by one-way analysis of variance (ANOVA) with Tukey-Kramer multiple comparisons post test for parametric data as indicated. $P<0.05$ was considered statistically significant.

Experimental Results

In a first example, C57BL/6 cells were cultured for 7 days with or without β-Caryophyllene. Culture with β-Caryophyllene suppressed differentiation of bone marrow cells to adipocytes.

In a second example, to determine the effects of β-caryophyllene on adipogenesis in bone marrow culture in vitro, bone marrow cells obtained from normal wild mouse were cultured in a medium containing either vehicle or differentiation medium (DM) with or without insulin in the presence or absence of β-caryophyllene (0.1-100 μM) for 7 days. Culture with β-caryophyllene (0.1-100 μM) suppressed differentiation of from bone marrow cells to adipocytes (FIG. 1). This effect was also seen when bone marrow cells were cultured in the presence of β-caryophyllene for 3 days and replaced to medium without β-caryophyllene and were cultured for additional 4 days (data were not shown). β-Caryophyllene was found to suppress adipogenesis in bone marrow cell culture in vitro. This was a first time finding.

In a third example, C57BL/6 cells were cultured for 18 days with or without β-Caryophyllene in a medium containing either vehicle or mineralization medium. Culture with β-Caryophyllene stimulated osteoblastic mineralization. Stimulation was also seen in culture with β-Caryophyllene for 7 days and replacement to medium without β-Caryophyllene for an additional 11 days.

In a fourth example, C57BL/6 cells were cultured for 7 days with β-Caryophyllene in a medium containing Tumor necrosis factor-α. Culture with β-Caryophyllene suppressed osteoclastogenesis. Cells cultured in Tumor necrosis factor-α with or without β-Caryophyllene and then cultured without β-Caryophyllene for an additional 4 days also exhibited suppression of osteoclastogenesis.

Based on the above experiments, it may be concluded that β-Caryophyllene has significant effects on adipogenesis and osteoblastic mineralization in bone marrow culture in vitro. Results also indicate that β-Caryophyllene has the effect of suppressing osteoclastogenesis. Accordingly, the experiments demonstrate that β-Caryophyllene can have potential effects on the differentiation of bone marrow mesenchymal stem cells to osteoblasts and suppress the differentiation to adipocytes.

* * *

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method for treating osteoporosis in a human being in need thereof comprising administering to said human being a therapeutically effective amount of β-Caryophyllene.

2. A method of stimulating osteoblastic mineralization in a human being in need thereof comprising administering to said human being a therapeutically effective amount of β-Caryophyllene.

3. A method of suppressing osteoclastogenesis or adipogenesis in a human being in need thereof comprising administering to said human being a therapeutically effective amount of β-Caryophyllene.

4. The method of claim 1 comprising administering a therapeutically effective amount of β-Caryophyllene of from about 25 mg to about 1000 mg per day.

5. The method of claim 1 comprising administering a therapeutically effective amount of β-Caryophyllene of from about 50 to about 300 mg per day.

6. The method of claim 1 wherein said therapeutically effective amount is effective to suppress differentiation of mesenchymal stem cells to adipocytes.

7. The method of claim 1 wherein said therapeutically effective amount is effective to favor osteoblastic bone formulation over the inhibition of osteoclastic bone resorption.

8. The method of claim 1 wherein said therapeutically effective amount is effective to favor osteoblastic bone formulation over the suppression of osteoclastogenesis or adipogenesis.

9. The method of claim 1 further comprising administering a therapeutically effective amount of a second therapeutic agent selected from the group consisting of genistein, vitamin D3, calcium, zinc, and combinations thereof.

10. The method of claim 1 further comprising administering to said human being from about 25 to about 110 mg of genistein per day.

11. The method of claim 1 further comprising administering to said human being about 54 mg of genistein per day.

12. The method of claim 1 further comprising administering to said human being about 400 IU of vitamin D3 per day.

13. The method of claim 1 further comprising administering to said human being about 8 mg of zinc per day.

* * * * *